United States Patent
Strandqvist et al.

(10) Patent No.: US 9,850,604 B2
(45) Date of Patent: Dec. 26, 2017

(54) NONWOVEN MATERIAL AND A METHOD FOR PRODUCING NONWOVEN MATERIAL

(71) Applicant: SCA HYGIENE PRODUCTS AB, Göteborg (SE)

(72) Inventors: Mikael Strandqvist, Lindome (SE); Hannu Ahoniemi, Landvetter (SE); Daniel Burman, Molndal (SE)

(73) Assignee: SCA Hygiene Products AB, Göteborg (SE)

( * ) Notice: Subject to any disclaimer, the term of this patent is extended or adjusted under 35 U.S.C. 154(b) by 87 days.

(21) Appl. No.: 14/618,766

(22) Filed: Feb. 10, 2015

(65) Prior Publication Data
US 2015/0250373 A1 Sep. 10, 2015

Related U.S. Application Data

(63) Continuation of application No. 12/096,189, filed as application No. PCT/SE2005/001850 on Dec. 7, 2005, now abandoned.

(51) Int. Cl.
*D04H 1/495* (2012.01)
*D04H 1/492* (2012.01)
(Continued)

(52) U.S. Cl.
CPC ....... *D04H 1/495* (2013.01); *A61F 13/15577* (2013.01); *D04H 1/492* (2013.01);
(Continued)

(58) Field of Classification Search
CPC ........ D04H 1/465; D04H 1/492; D04H 1/495; D04H 5/03; D04H 18/04; D04H 1/005;
(Continued)

(56) References Cited

U.S. PATENT DOCUMENTS 2,862,251 A * 12/1958 Kalwaites ............... D21F 11/00
162/114
3,485,708 A * 12/1969 Ballou ..................... D04H 3/05
162/115
(Continued)

FOREIGN PATENT DOCUMENTS

CA 841938 5/1970
CN 1364448 8/2002
(Continued)

OTHER PUBLICATIONS

Russian Decision on Grant (English Translation) issued in RU Application No. 2008127402/14.
(Continued)

*Primary Examiner* — Amy Vanatta
(74) *Attorney, Agent, or Firm* — Drinker Biddle & Reath LLP

(57) ABSTRACT

The present invention relates to a nonwoven material for use as an absorbent wiping material produced by hydroentangling of a substrate web comprising at least one layer of fibers selected from amongst synthetic fibers, regenerated fibers and natural fibers, wherein the nonwoven material (1) has a base level $h_0$ with protuberances (2, 3) on one side, wherein the protuberances (2, 3) form at least a first and a second surface structure respectively in the form of first (2) and second (3) protuberances from the base level $h_0$, wherein the first protuberances (2) have a height $h_1$ from the base level $h_0$ and the second protuberances (3) have a height $h_2$ from the base level $h_0$, where $h_2$ is higher than $h_1$, and each of the second protuberances (3) occupies an area of the surface of the base level at least 4 times greater than each of the first protuberances (2). The present invention also relates to a method for producing a nonwoven material (111), wherein hydroentangling of a substrate web (101), which comprises natural fibers having a length of less than 10 mm,
(Continued)

takes place on a surface-shaped carrier device (109) containing holes which form at least a first and a second pattern in the form of first and second holes respectively, wherein the second holes are at least 4 times larger than the first holes.

16 Claims, 7 Drawing Sheets

(51) Int. Cl.
| | | |
|---|---|---|
| *D04H 1/498* | (2012.01) | |
| *D04H 1/732* | (2012.01) | |
| *D04H 3/11* | (2012.01) | |
| *D04H 3/16* | (2006.01) | |
| *D04H 5/03* | (2012.01) | |
| *A61F 13/15* | (2006.01) | |

(52) U.S. Cl.
CPC .............. *D04H 1/498* (2013.01); *D04H 1/732* (2013.01); *D04H 3/11* (2013.01); *D04H 3/16* (2013.01); *D04H 5/03* (2013.01); *A61F 2013/15983* (2013.01); *Y10T 442/608* (2015.04)

(58) Field of Classification Search
CPC .......... D04H 1/732; D04H 1/498; D04H 3/11; D04H 3/16; D04H 13/003; D04H 18/00; A61F 2013/15715; A61F 2013/15983; A61F 13/15577; A61F 13/15617; A61F 13/15707; A61F 13/15731
USPC .......................................... 28/104, 105, 106
See application file for complete search history.

(56) References Cited

U.S. PATENT DOCUMENTS

| | | | | |
|---|---|---|---|---|
| 3,679,535 A | * | 7/1972 | Kalwaites ................ | D04H 1/74 28/105 |
| 3,679,536 A | * | 7/1972 | Kalwaites ................ | D04H 1/74 28/105 |
| 3,681,182 A | * | 8/1972 | Kalwaites ............. | D04H 1/736 28/105 |
| 3,750,237 A | * | 8/1973 | Kalwaites ................ | D04H 1/74 28/105 |
| 4,144,370 A | * | 3/1979 | Boulton .................... | B32B 5/10 162/115 |
| 5,144,729 A | * | 9/1992 | Austin ..................... | B32B 5/26 28/105 |
| 5,274,893 A | * | 1/1994 | Kitamura ................ | B29C 43/48 28/105 |
| 5,475,903 A | | 12/1995 | Collins | |
| 5,525,397 A | | 6/1996 | Shizuno et al. | |
| 5,618,610 A | * | 4/1997 | Tomita ................... | D04H 1/498 28/104 |
| 2002/0034914 A1 | | 3/2002 | DeLeon et al. | |
| 2002/0052582 A1 | | 5/2002 | Takai et al. | |
| 2003/0008108 A1 | | 1/2003 | Shizuno et al. | |
| 2003/0114071 A1 | | 6/2003 | Everhart et al. | |
| 2004/0121120 A1 | | 6/2004 | Gray et al. | |
| 2006/0063456 A1 | | 3/2006 | Carter | |
| 2007/0128411 A1 | * | 6/2007 | Kawai ..................... | A47L 13/16 428/170 |
| 2008/0028581 A1 | * | 2/2008 | Ronzani ................ | D04H 18/04 28/104 |

FOREIGN PATENT DOCUMENTS

| | | |
|---|---|---|
| EP | 0 625 602 | 11/1994 |
| EP | 1 022 003 A1 | 7/2000 |
| EP | 1 338 262 | 8/2003 |
| GB | 1088376 A | 10/1967 |
| GB | 2 335 627 | 9/1999 |
| RU | 2195910 C2 | 10/2003 |
| WO | 98/07914 A1 | 2/1998 |
| WO | 98/25560 | 6/1998 |
| WO | WO 01/41622 A2 | 6/2001 |
| WO | 02/04729 | 1/2002 |
| WO | 03/083197 | 10/2003 |
| WO | WO 2004-073479 A2 | 9/2004 |

OTHER PUBLICATIONS

International Search Report dated Jul. 7, 2006 issued in PCT Application No. PCT/SE2005/001850.
European Search Report dated May 27, 2010, in EP Application No. EP 05 81 5805.
Chinese Office Action dated Jul. 7, 2010, from corresponding patent application No. CN 200580052254.7.
Supplemental European Search Report dated Jul. 4, 2012 issued in European Patent Application 05 813 568.2.

* cited by examiner

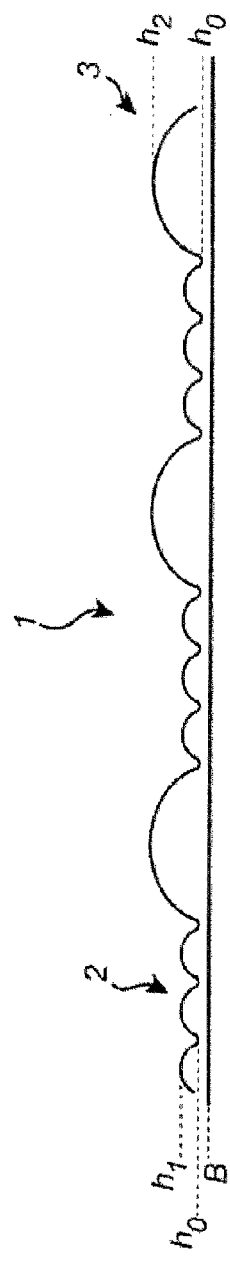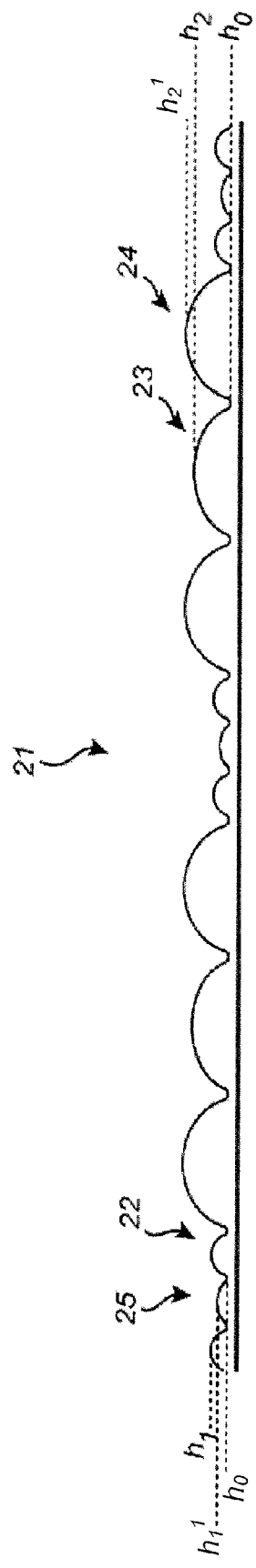

NONWOVEN MATERIAL AND A METHOD FOR PRODUCING NONWOVEN MATERIAL

This is a continuation application of copending application Ser. No. 12/096,189, having a §371 date of Jun. 5, 2008, which is a national stage filing based on PCT International Application No. PCT/SE2005/001850 filed on Dec. 7, 2005. The copending application Ser. No. 12/096,189 is incorporated by reference herein in its entirety.

TECHNICAL FIELD

The present invention relates to nonwoven material for use as an absorbent wiping material and a method for producing nonwoven material.

BACKGROUND ART

Absorbent nonwoven material is often used as a wiping material. It can be used to wipe up spillages and leakages in industrial, catering, office, hospital and domestic environments. There is often a desire to provide such materials with an image or decoration, for example a logotype. One common method of making images or decorations on nonwoven materials is to emboss images, the fibres are compressed by an embossing stamp. The use of thermal embossing means that a number of fibres are caused to melt and are damaged, which reduces the softness of the surface, and this in turn impairs the strength characteristics of the material. The embossed image will also be situated beneath the base level of the nonwoven material, which leads to the image being less readily visible.

Images or decorations in nonwoven material can also be produced by hydroentangling. This can be done, for example, by means of hydroentangling against an image transfer surface. A substrate web of fibres is laid on the image transfer surface, the substrate web is hydroentangled, that is to say it is sprayed with jets of liquid. The image transfer surface can be in the form of a wire gauze or a plate that exhibits depressions and/or projections. The nonwoven material receives its image or decoration against the wire gauze or the plate by being formed respectively against depressions and projections with the help of jets of liquid, and the nonwoven material receives an image or a decoration on both sides. A method of this kind is described in WO 02/04729. A nonwoven material produced in accordance with this method exhibits certain shortcomings with regard to liquid distribution and absorption, wiping on uneven surfaces and wiping of materials of different characters. Moreover, the resulting image is not so clear.

Another method for hydroentangling is described in WO 03/083197, where a nonwoven material with protuberances is produced. In this case, a plastic gauze is used as the carrier device for a web of fibres when it is hydroentangled. Here, too, a clear image is not obtained in the material, and it exhibits shortcomings with regard to liquid distribution and absorption, wiping of materials with different characters and wiping on uneven surfaces.

The intention of the invention is to solve the above problems and to make available improved wiping materials made of nonwoven material.

SUMMARY OF INVENTION

The object of the present invention is to make available a strong nonwoven material that possesses good absorption characteristics and wiping characteristics, and in addition has clear images in the form of decorative surface structures or decorations.

This is achieved by the invention with a nonwoven material intended for use as an absorbent wiping material produced by the hydroentangling of a substrate web comprising at least one layer of fibres selected from amongst synthetic fibres, regenerated fibres and natural fibres, wherein the nonwoven material has a base level with protuberances on one side. The protuberances form at least a first and a second surface structure respectively in the form of first and second protuberances from the base level, wherein the first protuberances have a height $h_1$ from the base level and the second protuberances have a height $h_2$ from the base level, where $h_2$ is higher than $h_1$, and each of the second protuberances occupies an area of the surface of the base level at least 4 times greater than each of the first protuberances.

Furthermore, a method is proposed for producing a nonwoven material by hydroentangling a substrate web of fibres selected from amongst synthetic fibres, regenerated fibres and natural fibres. The method involves the steps of transferring the substrate web, which comprises natural fibres having a length of less than 10 mm, to a surface-shaped carrier device containing holes which form at least a first and a second pattern in the form of first and second holes respectively, wherein the second holes are at least 4 times larger than the first holes, and of hydroentangling the substrate web on the carrier device by means of jets of liquid under high pressure, so that the fibres of the substrate web penetrate down into the holes.

BRIEF DESCRIPTION OF DRAWINGS

The invention is now described below in greater detail with reference to the following Figures:

FIG. 1 shows a cross-sectional view of a nonwoven material in accordance with the invention.

FIG. 2 shows a cross-sectional view of a further nonwoven material in accordance with the invention.

DETAILED DESCRIPTION OF THE INVENTION

An embodiment of a nonwoven material in accordance with the invention is shown in FIG. 1. The present invention thus relates to a nonwoven material 1 for use as an absorbent wiping material, produced by hydroentangling of a substrate web comprising at least one layer of fibres selected from amongst synthetic fibres, regenerated fibres and natural fibres, wherein the nonwoven material 1 has a base level $h_0$ with protuberances 2, 3 on one side, wherein the protuberances 2, 3 constitute at least one first and one second surface structure respectively in the form of first and second protuberances 2, 3 from the base level $h_0$, wherein the first protuberances 2 have a height $h_1$ from the base level $h_0$ and the second protuberances 3 have a height $h_2$ from the base level $h_0$, where $h_2$ is higher than $h_1$, and each of the second protuberances 3 occupies an area of the surface of the base level at least 4 times greater than each of the first protuberances 2.

The expressions "hydroentangling" or "spunlacing" are used here to denote that fibres are tangled together by means of very fine jets of liquid under high pressure. Several rows of jets of liquid are directed at the fibre web or the substrate web, which is supported by a wire gauze or a drum. The entangled web is then dried. A nonwoven material with a well-integrated composition is obtained as a result.

Figure 3:
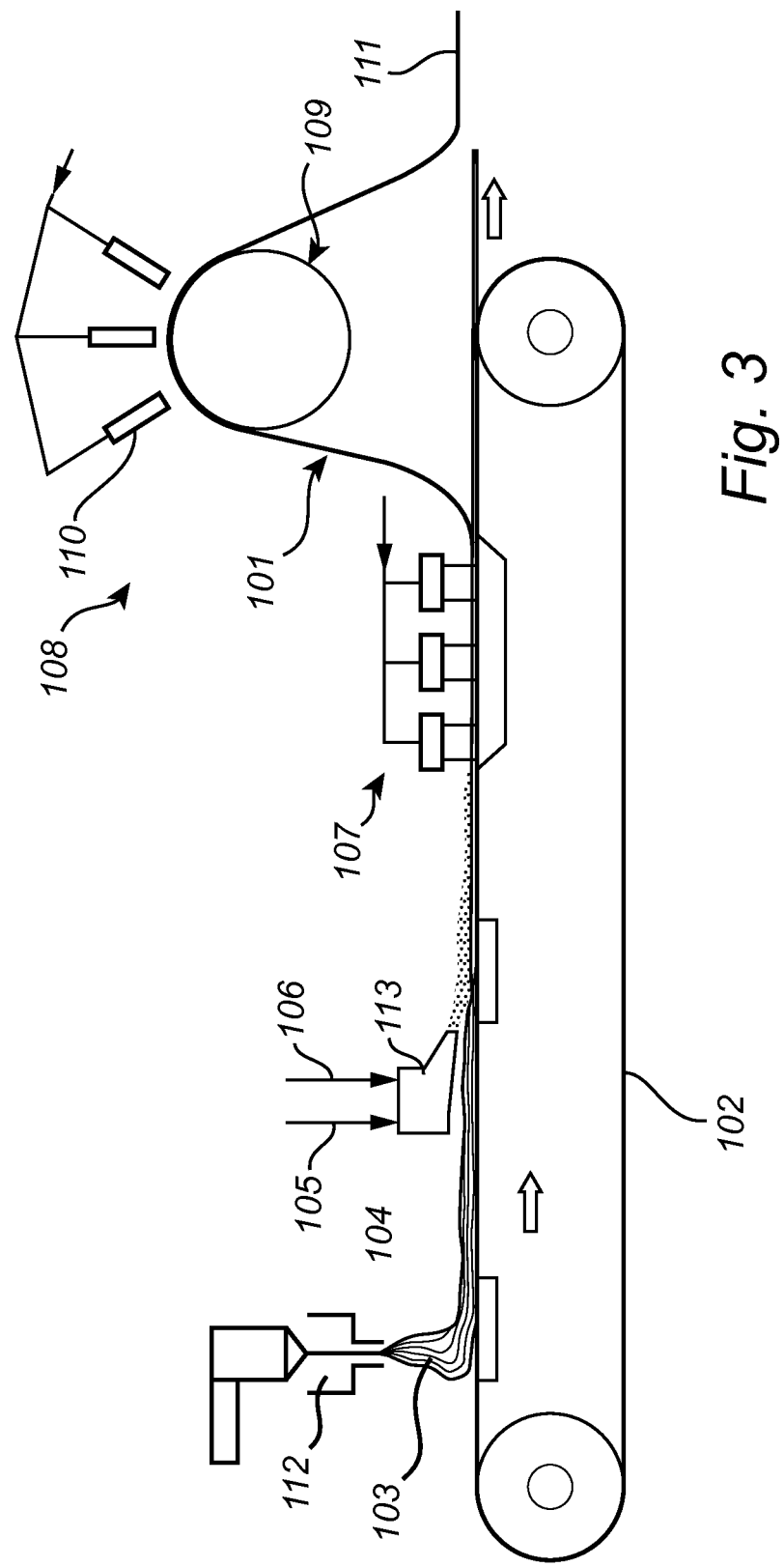
FIG. 3 illustrates schematically an embodiment of an arrangement for producing nonwoven material in accordance with the invention.

Also proposed in accordance with the present invention is a method, which can be seen in hydroentangling stage 108 in FIG. 3, for producing a nonwoven material 111 by hydroentangling a substrate web 101 of fibres selected from amongst synthetic fibres, regenerated fibres and natural fibres, wherein it includes the following steps:
a) transferring the substrate web 101, which comprises natural fibres having a length of less than 10 mm, to a surface-shaped carrier device 109 containing holes which form at least a first and a second pattern in the form of first and second holes respectively, wherein the second holes are at least 4 times larger than the first holes, and
b) hydroentangling the substrate web 101 on the carrier device 109 by means of jets of liquid under high pressure, so that the fibres of the substrate web 101 penetrate down into the holes. The hydroentangling process utilizes conventional pressures and hole diameters in nozzles in the arrangement. Details of conventional parameters can be found in, for example, CA 841 938.

The proportion of natural fibres having a length of less than 10 mm used in the method is preferably at least 5% by weight.

The expression "substrate web" denotes a pre-formed fibre web that is capable of being produced by one or other conventional means. Fibres are laid down onto a forming wire gauze. Continuous filaments are laid down, for example, by the meltblown or spunlaid technique, and staple fibres and pulp fibres can be wet-laid or dry-laid.

The expression "carrier device" is used here to denote the device which supports the substrate web when it is hydroentangled, and this serves the purpose at the same time of imparting an image/structure to the nonwoven material. The carrier device should be made of a material that is sufficiently hard for hydroentangling, that is to say it should be inflexible during the hydroentangling stage. Plate or nickel plate are suitable materials.

The expression "surface-shaped" denotes that the carrier device exhibits a plane and uniform surface, for example in the form of a sheet material. This can consist of a sheet of plate with holes of different sizes. The sheet has a uniform and plane surface, which we define as "surface-shaped". Holes are arranged on this surface-shaped carrier device. The sheet of plate can be formed as a drum, although it has no separate projections or depressions, but the sheet of plate is "surface-shaped" or two-dimensional with holes.

There now follows a description of an example of the production of a nonwoven material in accordance with the present invention, wherein the production of the substrate web is also described, as illustrated schematically in FIG. 3. Provided for the production of the substrate web 101 is an endless forming wire gauze 102, onto which continuous filaments 103 can be laid down, and any surplus air is sucked down through the forming wire gauze 102, in order to form a layer 104 of a substrate web. The forming wire gauze 102 is caused to advance together with the continuous filaments to a wet-laying stage, where a slurry consisting of a mixture of natural fibres 105 and staple fibres 106 is wet-laid onto, and partially into, the layer 104 of continuous filaments in the substrate web, and any surplus liquid is drained off by the forming wire gauze 102. The substrate web can then be bonded together in such a way that it holds together in a satisfactory fashion for further processing. Bonding can be effected by pre-hydroentangling, as illustrated by way of example in stage 107 in FIG. 3. The forming wire gauze 102 conveys the substrate web 101 to the hydroentangling stage 108, where the substrate web 101
a) is transferred to a carrier device 109 containing holes which form at least a first and a second pattern in the form of first and second holes respectively, wherein the second holes are larger than the first holes, and
b) is hydroentangled on the carrier device 109 by means of jets of liquid under high pressure, so that the fibres of the substrate web 101 penetrate down into the holes.

Nozzles 110 for jets of liquid are shown in the hydroentangling stage 108. In the hydroentangling stage, the filaments and the fibres are mixed thoroughly together and are bonded to a nonwoven material 111 by the effect of many fine jets of liquid under high pressure, which strike the fibres in order to mix them and tangle them together with one another. The water is drained away through the holes in the carrier device 109. After hydroentangling, the nonwoven material 111 is conveyed to a drying stage (not shown).

The hydroentangling stage for the surface structure can take place alternatively on a wire gauze loop. The drum or the loop is covered with a suitable surface-shaped material containing holes in accordance with the invention and constitutes a carrier device.

The number of nozzles per drum is around 1 to 3, although a larger number of nozzles can also be present.

Bonding can take place in a pre-hydroentangling stage 107, which precedes the hydroentangling 108 on the carrier device 109 in accordance with the invention. Pre-hydroentangling intended for bonding of the substrate web can take place on one or both sides of the substrate web. In the case of hydroentangling on both sides, for example, two drums positioned one after the other can be used, where one side of the substrate web is pre-hydroentangled on the first drum, and the second side is pre-hydroentangled on the second drum.

When specific materials or compositions of materials are used, pre-bonding of the substrate web, for example in the form of pre-hydro entangling, may be necessary. The substrate web must hold together sufficiently well to enable it to be moved to the hydroentangling stage on the carrier device when the substrate web is to be given its surface structure.

In accordance with the embodiment illustrated in FIG. 3, the filaments 103 are produced from extruded molten plastic that is laid down directly onto the forming wire gauze 102. The filaments 103 can be cooled with air 112 to enable them to solidify before they come into contact in order to form a non-bonded layer 104. The natural fibres 105 and the staple fibres 106 are suspended in a conventional way, either together or individually, and are then mixed and wet-laid onto the layer 104 on the substrate web. The mixture is pumped out from a flow box 113 for wet-laying. Surplus liquid is sucked out through the forming wire gauze 102. The method of producing the substrate web is shown here for illustrative purposes only, and it is not restrictive. For example, it is possible to form a substrate web that does not have continuous fibres. For example, the stage at which continuous filaments 103 are laid down is not necessary in this case. The method in accordance with the invention relates essentially to the hydroentanglement stage of a substrate web.

The carrier device can be manufactured from a metal plate or a sheet of sufficient hardness to enable it to function as a support in conjunction with hydroentangling. The plate or the sheet must exhibit a plane and uniform surface, and it must contain the holes that are intended to impart the surface structure. It is preferable for the carrier device to be formed as a cylinder.

A nonwoven material in accordance with the invention is obtained by the new method. A nonwoven material of this kind has protuberances of different heights, and these protuberances occupy different areas of the surface of the base level of the nonwoven material. This results in a nonwoven material with a good liquid distribution, absorption capacity and good comfort during use, advantages that are described in greater detail below. The hydroentangling of the fibres causes the quantity of fibres to vary between protuberances with a different height and surface extent in the base level and the material in the rest of the nonwoven material. The expression "rest of the nonwoven material" is used to denote those parts that lie between the protuberances in the extent of the plane of the nonwoven material. The variation of the fibres depends both on the pressure in the jets of liquid and on the composition of the fibres in the material. Different fibres are caused to move with greater or lesser ease by the act of spraying liquid against the substrate web on the carrier device. Short fibres are able to move more easily, for example. This results in a nonwoven material with a good capacity to absorb different materials. Hydroentangling also results in the creation of a strong nonwoven material.

Since the method involves the transfer of a substrate web which contains natural fibres having a length of less than 10 mm, these fibres will be mobile in the fibre network. This leads to good integration and gives distinct and good surface structures in the nonwoven material that is produced. It also means that a relatively high proportion of natural fibres can be used in the method for producing nonwoven material in accordance with the invention.

In accordance with previously disclosed hydroentangling, the image transfer surface has exhibited depressions and/or projections of the kind disclosed in WO 02/04729, for example. An image transfer surface of this kind can be regarded as three-dimensional. When nonwoven material is formed against a depression in the image transfer surface, a depression is formed on one side and a corresponding raised area on the other side. The opposite applies in the case of forming against a projection on the image transfer surface. A carrier device which transfers surface structures to the nonwoven material is used with the invention. The carrier device can be a plate, for example a nickel plate. The carrier device can be extended as a web or can form a drum. Compared with previously disclosed technology, which utilizes a three-dimensional image transfer surface, the carrier device in accordance with the invention is regarded as being surface-shaped or two-dimensional in the sense that it does not have any projections or depressions. It has a plane and uniform surface. In the case of a plate, it consists of a sheet of plate with holes of different sizes. The sheet of plate can be formed as a drum, although it does not possess any separate projections or depressions. Described in WO 03/083197, as previously mentioned, is a method for hydroentangling on a plastic gauze which contains holes. In conjunction with this, protuberances with the same height and size are produced in the nonwoven material. According to the present invention, protuberances are produced where second protuberances occupy an area of the base level at least 4 times larger than in the case of the first protuberances, where the protuberances have different heights. Protuberances of this kind in a nonwoven material are not produced in WO 03/083197.

Before hydroentangling takes place, in which the surface structure is produced, pre-hydroentangling can be performed as described above. In conjunction with this, pre-hydroentangling is able to cause bonding together of the substrate web, which can take place on both sides of the substrate web.

In the course of the hydroentangling, for the purpose of forming the surface structure, water or some other liquid is sprayed at high pressure onto the substrate web that is supported against the carrier device. These water jets bring about entangling of the substrate web, that is to say tangling together of the fibres. A nonwoven material with a well-integrated composition is produced. The appropriate pressure in the entangling nozzles is adapted according to the fibre material, the weight per unit area of the substrate web, etc. The fibres in the substrate web will become tangled together, that is to say the nonwoven material is bonded together, at the same time as a surface structure is formed on the nonwoven material when entangling takes place against the carrier device in accordance with the invention. The pressure exerted by the water jets is so high that the fibres are caused to be displaced on the carrier device, and they will penetrate down into the holes. The ability to penetrate down into the holes depends in part on the physical size of the holes. A larger hole will permit the fibres to penetrate further down into the holes. This results in protuberances with different heights $h_1$ and $h_2$ on the nonwoven material. Dewatering takes place in conjunction with the forming of the protuberances, and the water is drained away through the same holes in which the protuberances are formed. This results in the fibres moving easily on the carrier device and being displaced towards the holes and down into the holes. The fibres on the carrier device that are present in association with the fibres that are drawn down into the holes will accompany them, and this will lead to the other side of the resulting nonwoven material exhibiting an essentially smooth surface.

The use of hydroentangling of the nonwoven material to impart surface structures produces a softer and more textile-like material with good strength characteristics. The tangling together of the fibres in the hydroentangling process provides a good mechanical bond between the fibres, and good strength of the nonwoven material is achieved in this way. Moreover, the fibres are not damaged in conjunction with bonding together, as occurs in the case of thermal embossing, for example. A soft and textile-like material is of great importance for absorbent wiping materials that will be used for wiping up. The material will be soft and smooth, that is to say comfortable to hold during use. A textile-like wiping material is also more attractive to look at, and a product which gives the impression of very high quality and strength is obtained.

At least two surface structures in the form of two protuberances 2, 3 are contained in nonwoven material, one background structure and one principal structure. The protuberances in the structures exhibit different heights $h_1$ and $h_2$. The background structure has a lower height $h_1$, since it is not the predominant surface structure.

The different heights of the surface structures mean that the base level of the nonwoven material will not always come into direct contact with the object to be wiped. This can be the skin of a user, the surface of a base to be wiped, etc. Particles of different sizes can be picked up by the absorbent wiping material. Slightly larger particles, which might otherwise have "slipped" away from a flat nonwoven material, will be capable of being picked up in a protuberance. The fact that the protuberances have different heights means that particles of different sizes are picked up by protuberances of different heights. A better "carrying capacity" is achieved. The protuberances will also make it easier to wipe places that are not readily accessible, such as corners or angles. The protuberances are able to extend slightly further inwards than would otherwise have been possible with a flat nonwoven material. It is also easier to wipe uneven surfaces that are slightly rough, because the protuberances are able to reach down into the areas of roughness. Since the nonwoven material will have a number of different levels above the base level of the nonwoven material, the highest protuberances with a height $h_2$ will be able to reach further down into the areas of roughness in the ground, whereas the lower protuberances with a height $h_1$ will not reach as far down. Improved wiping up will be achieved as a result.

Good absorption capacity and liquid distribution are also obtained. The quantity of fibres will vary between protuberances of different heights and extents and the material in the base level. This in turn leads to different pore sizes in different areas of the nonwoven material. The pore volume distribution obtained on the side with a surface structure is thus broader than on a side without a surface structure and protuberances or with only a single surface structure. Larger pores have the ability, for example, to contribute to the better absorption of highly viscous substances and a better retaining ability in the material. In accordance with the present invention, the second protuberances occupy an area of the surface of the base level of the nonwoven material at least 4 times greater than the first protuberances. The protuberances with the height $h_2$, that is to say with the highest height, occupy the greatest area. The fourfold difference in size accordingly gives rise to protuberances that are larger in terms of both their height and their extent. The difference in size leads to the following effects, among other things. The protuberances exhibit an excellent absorption capacity, in particular for highly viscous substances, and the nonwoven material will possess good wiping-up characteristics. The larger areas of the protuberances also lead to significant differences in the appearance of the different surface structures. The material obtained in accordance with the invention is also soft, at the same time as it is smooth and flexible, due to the fact that the nonwoven material is hydroentangled.

In addition, one of the purposes of the surface structures is to be decorative, for example. The protuberances in the surface structures can have any desired form. The protuberances can be circular, elliptical, triangular, square, etc. These can also be combined to form an image. This may be a logotype, for example, some kind of information for the user that may be of assistance in relation to the method of use, for instance, or simply a decorative image, for example flowers, hearts, leaves, feathers, etc. A more refined product is obtained with two different surface structures. On the one hand, a distinct image is obtained in the form of the principal structure. The background structure provides a more complete image of a product, with a textile-like appearance that imparts a better feel than a smooth material. This gives the impression of increased absorption and strength.

Figure 4:
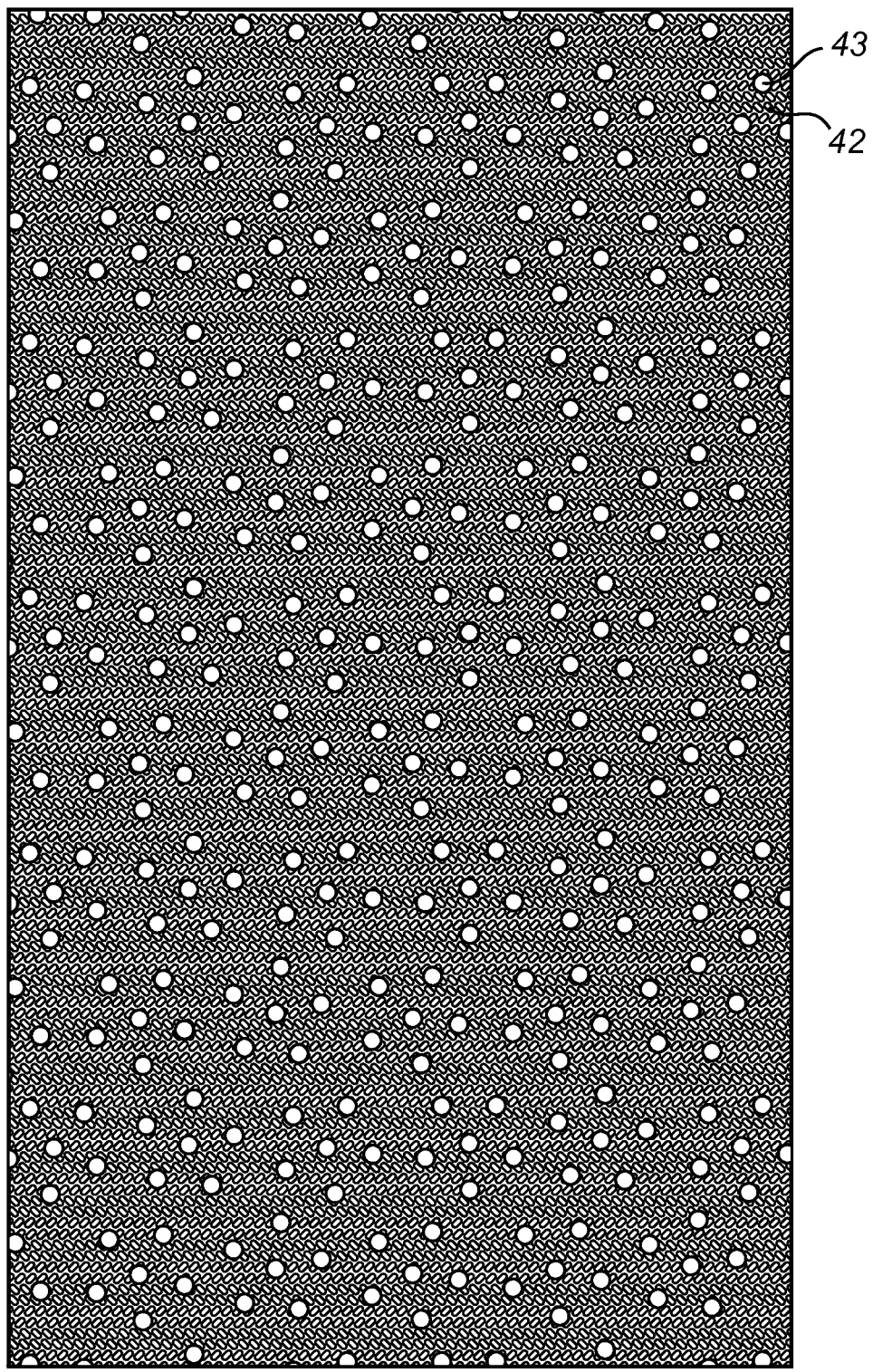
FIG. 4 illustrates an embodiment of a plate of a carrier device viewed from above, which is used in the method in accordance with the present invention.

An embodiment of a plate that is used in accordance with the invention is shown here in FIG. 4 to illustrate how the holes are distributed over a plate. In order to illustrate the plate, the holes are indicated as white, and the plate itself is black in the Figure. Illustrated here are the smaller holes 42, which constitute the first holes 42 which form the first pattern, and the larger holes 43, which constitute the second holes 43 and form the second pattern. The second pattern thus constitutes of the circular holes 43, which are grouped in a regular pattern, although this is not essential for the invention. An irregular pattern can also be possible. The first pattern is the background pattern, which consists of the small holes 42, which can also be a regular or an irregular pattern. The protuberances that are fanned against the smaller holes 42 will constitute a background structure in the nonwoven material in accordance with the present invention, while the protuberances that are formed against the larger holes 43 will constitute a principal structure.

In accordance with the method, the carrier device contains holes 42, 43 which form patterns, whereas the nonwoven material contains protuberances 2, 3 which form surface structures. The patterns and the surface structures correspond to one another in the sense that the pattern that is present on the carrier device creates the surface structure on the nonwoven material. The first and the second pattern respectively will provide the first and the second surface structure of the nonwoven material.

In accordance with the invention, the second side of the nonwoven material is preferably essentially smooth. As can be appreciated from FIG. 1, the smooth side can be regarded as a bottom level B in the nonwoven material in relation to the base level $h_0$ and the protuberances 2, 3 on the first side. The essentially smooth side of the nonwoven material can be used for wiping if this is more appropriate, for example when wiping up a liquid with low viscosity.

In the nonwoven material in accordance with the present invention, each of the second protuberances occupies an area of the surface of the base level at least 4 times greater than each of the first protuberances. This is achieved by the method in accordance with the present invention, wherein the second holes are at least 4 times larger than the first holes. A certain difference in size between the holes in the carrier device is required in order for a difference in height to be capable of being achieved in the protuberances in the nonwoven material. On the basis of the at least fourfold difference in size, this gives the difference in height that is sought in accordance with the present invention. The resulting nonwoven material exhibits advantageous absorption characteristics thanks to the pore volume distribution and the protuberances of different sizes, and the surface structures will be particularly clearly visible thanks to the difference in sizes. The greater the relationship that exists between the area of the base level occupied by the first protuberances and the second protuberances, the greater will be the difference in height between the protuberances, and the better will be the effects that can be achieved, that is to say better pore size distribution, better absorption, and even more distinct patterns. The geometrical design of the holes can govern the differences in height to a certain extent. For example, a narrow and elongated hole will be lower than a symmetrical hole if these occupy the same area. According to further embodiments, each of the second protuberances can occupy an area of the surface of the base level at least 8 times greater than each of the first protuberances in the nonwoven material in accordance with the present invention, and it is more preferable still for the second protuberances to occupy an area of the surface of the base level at least 12 times greater than each of the first protuberances. The second holes in the method can be at least 8 times larger than the first holes, and it is more preferable still for the second holes to be at least 12 times larger than the first holes. This leads to good absorption in the second surface structure, which is particularly clearly visible with this difference in size. The greatest difference in size is in the order of 50 times, although even 80 times larger may be possible, with regard to both the hole size and the area of the protuberances.

The height $h_1$ of the nonwoven material in accordance with the invention is preferably at least 200 µm, and the height $h_2$ is preferably at least 300 µm. In accordance with a preferred embodiment, the difference between $h_1$ and $h_2$ is at least 100 µm, and it is more preferable still for the difference between $h_1$ and $h_2$ to be at least 200 µm. Thanks to these heights and the difference in height, the contact and the wiping capacity are very good on uneven surfaces and in areas that are not readily accessible, in addition to which good liquid distribution and absorption are obtained. Highly distinct surface structures and particularly distinct differences are also obtained between the background structure and the principal structure.

The first protuberances preferably occupy an area of the surface of the base level of at least about 0.25 mm$^2$. A size of 0.25 mm$^2$ is required in order to be able to provide a background structure. The largest size is about 1.00 mm$^2$. Each of the second protuberances also occupies an area of the surface of the base level preferably of at least about 1.00 mm$^2$, which is four times 0.25, and the size of 1.00 mm$^2$ is required in order to be able to produce the desired effects. The second protuberances can have sizes of about 4-16 mm$^2$. They can also be as large as 20 mm$^2$. If the first protuberance occupies an area larger than 0.25 mm$^2$, the second protuberances will in turn occupy a larger area in order for the same effects to be capable of being achieved, that is to say at least 4 times larger than the area of the background pattern.

In accordance with the method, the second holes in the carrier device preferably exhibit a size of at least about 1.00 mm$^2$, and the first holes preferably exhibit a size of at least about 0.25 mm$^2$. The desired heights in the protuberances in the nonwoven material in accordance with the invention are achieved at these orders of size. Additional hole sizes correspond to the sizes of the protuberances referred to above.

Figure 5:
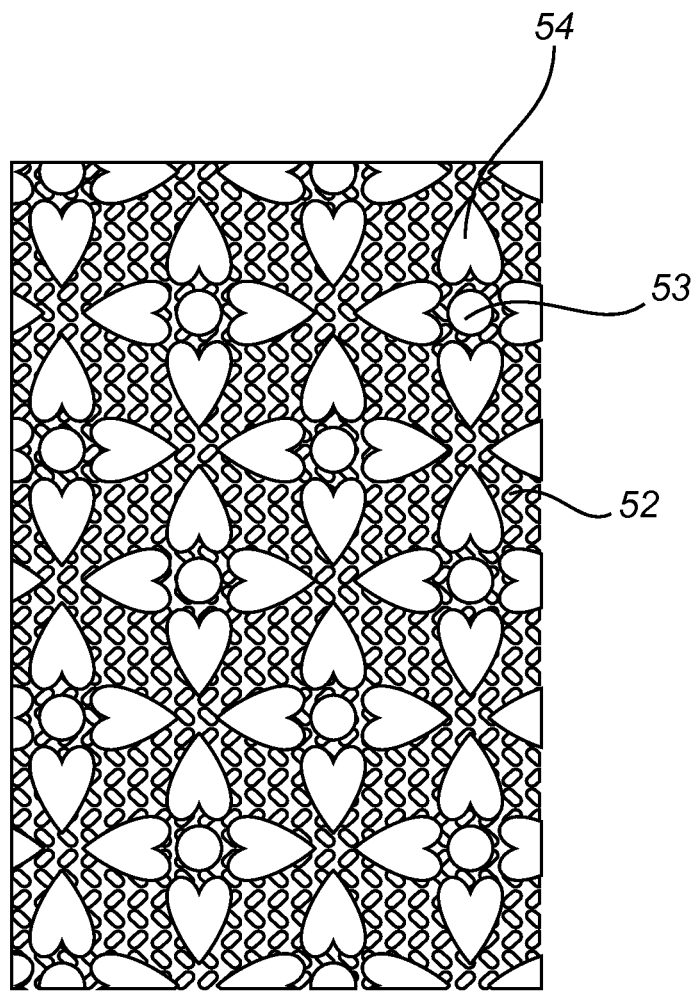
FIG. 5 illustrates a further embodiment of a plate of a carrier device viewed from above, which is used in the method in accordance with the present invention.

The nonwoven material in accordance with the present invention can have additional protuberances 24, FIG. 2, with at least an additional height $h_2^1$ from the base level $h_0$, wherein the height $h_2^1$ of the additional protuberance 24 is higher than $h_2$ and occupies a larger area of the surface of the base level than the protuberances 23 with the height $h_2$. An embodiment of this kind is illustrated in FIG. 2, for example. The nonwoven material has first protuberances 22 with a height $h_1$ and second protuberances 23 with a height $h_2$. Also present is a third protuberance 24 with a height $h_2^1$ that is higher than $h_2$, which constitutes a part of the second surface structure, that is to say it constitutes a part of the principal structure. Illustrated in FIG. 5 is a plate with the ability to produce a nonwoven material having three protuberances with the heights $h_1$, $h_2$ and $h_2^1$. A background pattern with smaller holes 52 is shown here. The larger holes constitute circular holes 53, which constitute a part of the principal pattern, which in this case is a floral pattern. The principal pattern also includes additional holes 54, in this case heart-shaped holes, of a size that is larger than the size of the holes 53. These constitute a part of the principal pattern. Present on a plate of this kind are protuberances with the height $h_1$ formed against the small holes 52, protuberances with a height $h_2$ formed against the holes 53, and protuberances with a height $h_2^1$ formed against the holes 54.

A nonwoven material containing protuberances with the additional height $h_2^1$ is produced in accordance with the method, where the carrier device has additional holes which are larger than the holes in the second patterns.

The nonwoven material 1 in accordance with the invention can also have additional protuberances 25 having at least an additional height $h_1^1$ from the base level $h_0$, in conjunction with which the height $h_1^1$ of the additional protuberance 25 is lower than $h_1$ and occupies a smaller area of the surface of the base level than the protuberances 22 with the height $h_1$. The protuberances 25 can also been seen in FIG. 2. A nonwoven material of this kind comprising additional protuberances with the height $h_1^1$ is produced in accordance with the method, in which the carrier device has additional holes that are smaller than the holes in the first patterns. Different sizes of the holes give different heights of the protuberances. The larger the hole, the higher the resulting protuberance.

Protuberances with heights between $h_1$ and $h_2$ can also occur, of course.

Additional surface structures can also be formed by protuberances with a different height and which occupy a different area of the surface of the base level than the protuberances with the heights $h_1$ and $h_2$. More heights offer the opportunity to wipe up additional particle sizes when wiping up materials, and an even broader pore size distribution can be achieved, which is beneficial for the absorption capacity and the ability to retain highly viscous substances in the protuberances. More advanced surface structures can be created in addition. This also contributes additionally to imparting a more textile-like appearance, which is very positive in products of this type.

The carrier device 109 can also have additional holes which are smaller than the holes in the first patterns. The nonwoven material obtained in this case comprises additional protuberances with a height $h_1^1$ that are lower than the protuberances with a height $h_1$.

Nonwoven material in accordance with the invention can comprise synthetic fibres, which are selected from amongst polyolefin, polyester and polyamide fibres and mixtures thereof. The polyolefins, for example, are polyethylene or polypropylene. An example of a polyester is polyactide. The fibres can be produced from homopolymers or copolymers or mixtures thereof. The material for the synthetic fibres can also be selected from amongst mono-, bi-, multi-components and mixtures thereof.

The fibres can also include regenerated fibres, which can be selected from amongst regenerated cellulose fibres such as rayon, viscous and lyocell.

The synthetic fibres are selected from amongst staple fibres, continuous filaments and mixtures thereof. Hydroentangling of fibres can be performed with both staple fibres and continuous filaments. An advantage associated with shorter fibres is that it is easier to create the desired surface structures. Continuous filaments require larger holes in the carrier device in order to be able to form protuberances.

Meltblown or spunlaid fibres are preferably selected from amongst the continuous filaments, and the most preferred are spunlaid fibres. They should preferably possess a coarseness of 1-3 dtex. The cross section of the fibres can be circular or trilobal, for example. Other cross sections are also conceivable.

When continuous filaments are used, the substrate web should preferably not be thermally bonded. The filaments will then be capable of being displaced more readily on the carrier device and of being laid down and penetrating down into the holes in the carrier device in conjunction with the entangling process. In spite of the preference for non thermally-bonded continuous filaments, the method will still function if the filaments are thermally bonded. Non-bonded filaments on the substrate web are achieved by cooling the fibres in conjunction with laying down to form a substrate web, so that they solidify before they come into contact with one another.

The staple fibres preferably have a length of at least 3 mm. Fibres with lengths of less than 3 mm are difficult to hydroentangle. They should preferably have a length not exceeding 60 mm, or not exceeding 50 mm. More preferable still, the staple fibres should have a length not exceeding 25 mm. The staple fibres preferably possess a coarseness of 1-3 dtex. If thin fibres are used, the length of the fibres should be quite short. Otherwise, the risk is present that the fibres will become tangled together in clumps. The cross section of the fibres may be circular, trilobal, star-shaped, hollow, etc.

The fibres can include micro fibres in the form of split fibres that are split at the hydroentangling stage, both continuous filaments and staple fibres, which possess a coarseness of less than 1 dtex. Such fine fibres give a smooth and soft product.

Nonwoven material in accordance with the invention can include natural fibres, which are selected from amongst cellulose fibres, pulp fibres, cotton fibres, ultimate flax fibres and mixtures thereof.

In accordance with one embodiment, the nonwoven material contains pulp fibres. The method in accordance with the invention preferably also includes pulp fibres in conjunction with hydroentangling. This is beneficial for the absorption capacity of the resulting nonwoven material, since pulp fibres possess a very good absorption capacity. The pulp fibres will be present in a higher proportion in the protuberances than in the rest of the nonwoven material. This is because these fibres are more mobile and exhibit the ability to participate in the entangling when the fibres are sprayed with water jets. Pulp fibres are irregular, flat, twisted and wavy, and they become pliable when wet. These characteristics mean that they can be easily mixed into and entangled with a web of continuous filaments and/or staple fibres. Pulp fibres and regenerated fibres also possess a low wet module, with the result that they are easier to bend in the wet condition. This is of benefit for hydroentangling. The resulting nonwoven material will thus contain a higher proportion of pulp fibres in the protuberances, with the highest proportion being present in the protuberances with the highest height and the largest area extent in the base level. In a wiping material made from a nonwoven material of this kind, rapid absorption will occur when the protuberances first come into contact with a liquid that is to be wiped up. Because pulp fibres are more opaque than synthetic fibres, for example, the proportionate increase in the protuberances will also result in the protuberances being much more clearly visible and in the production of a distinct image on the nonwoven material. The proportionate increase in pulp fibres in the protuberances also leads to a rapid and increased absorption capacity in the protuberances.

The total density of the fibres, which is measured in $g/cm^3$, may be lower in the protuberances. This is attributable to the fact that the hydroentangling process has not displaced sufficient fibres into the holes in the carrier device to compensate for the expansion that has taken place, with the result that the density is lower in the protuberances. The expression "expansion" is used here to denote that the fibres have been able to expand into the holes in the plate and, in so doing, into the protuberance in the material. Different fibres are displaced with different ease in conjunction with hydroentangling. Pulp fibres, for example, are displaced very easily, whereas longer fibres or continuous filaments may find it more difficult to be displaced into the holes. The resulting nonwoven material will then have wider pores in the protuberances, which is advantageous for the absorption of highly viscous liquids.

Nonwoven material can also include other ingredients in the form of polymers, additives, etc.

Preferred weights per unit area for the nonwoven material in accordance with the invention are at least 30 $g/cm^3$, or preferably 60 $g/cm^3$. The weight per unit area preferably does not exceed 120 $g/cm^3$, or more preferable still 100 $g/cm^3$. A relatively high weight per unit area is required in order to be able to create a distinct surface structure. The most preferable weight per unit area is ca. 80 $g/cm^3$.

In accordance with the invention, a preferred nonwoven material can contain 5-95% by weight of fluff pulp and 95-5% by weight of synthetic fibres. The synthetic fibres are preferably selected from amongst polypropylene fibres, polyethylene fibres, polyamide fibres and polyester fibres, where the polyester fibres may be polyethylene terephthalate fibres. In one embodiment, the synthetic fibres can also be combined with 5-95% by weight of viscose fibres. Furthermore, one embodiment can contain 20-80% by weight of fluff pulp or viscose fibres and 80-20% by weight of synthetic fibres.

In a preferred embodiment of the invention, the nonwoven material contains ca. 40% by weight of polyethylene terephthalate fibres having a coarseness of 1.5-2.3 dtex and a length of 15-20 mm, and ca. 60% by weight of fluff pulp.

The invention also includes nonwoven material containing fibres in several layers. These may be layers containing a number of different fibres or the same sort of fibres. A plurality of such layers may also be used to form a laminate. In the method in question, this means that the substrate web comprises several layers, or that several layers of substrate webs are transferred to the carrier device for hydroentangling. With the hydroentangling method that is used, with the drum as the base for producing the image or decoration, it is advantageous for the pulp fibres or regenerated fibres that they are hydroentangled down into the carrier material and, in so doing, form the desired three-dimensional surface structures. The fact that these fibres bend more easily can be attributed to their low wet module. In this case, the carrier material is the first layer, on top of which the next layer is laid.

The invention also relates to an absorbent wiping material that includes at least one nonwoven material in accordance with the invention, as described above. The nonwoven material can be combined with a similar nonwoven material or a different nonwoven material in accordance with the invention, but also, for example, with a different fibre composition or a different surface structure. The surface structures can be so arranged as to face away from one another, towards one another, or a smooth side can be so arranged as to face towards a side with a surface structure. Furthermore, the absorbent wiping material can include a suitable tissue material that is combined with the nonwoven material.

EXAMPLES

There now follow a number of examples of nonwoven materials produced in accordance with the present invention.

A substrate web is produced in the conventional way. The substrate web is then hydroentangled, wherein it is transferred to the carrier device in the form of a plate that is cylindrical in shape. The substrate web is hydroentangled with jets of water.

A number of different plates are used in production. Data for the background patterns of these plates are shown in Table 1. The area of individual holes in the background pattern has been measured. Here the area has been measured for the largest holes. The different holes can form part of an image, for example a flower. One example of a part of an image is illustrated below for a principal pattern in FIG. 5. If the background pattern contains a group of protuberances with different areas, which together constitute part of an image, for example a flower, these protuberances together constitute part of an image of a first surface structure that has been produced on a group of holes in a first pattern. The area of part of an image has also been measured.

Data for the principal patterns of these plates are shown in Table 2. The area of individual holes in the principal pattern has been measured here. The different holes can form part of an image, for example a flower. If the principal pattern contains a group of protuberances with different areas, which together constitute an image, these protuberances together constitute part of an image of a second surface structure that has been produced on a group of holes in a second pattern. Part of an image of a second surface structure in the form of a flower is illustrated in FIG. 5, for example. The area of part of an image has also been measured.

Table 3 shows the size relationship between holes in the principal pattern and the background pattern, that is to say between the second pattern and the first pattern. The size relationships are shown in respect of individual holes/individual holes.

Heights $h_1$ and $h_2$ measured in the nonwoven material that was produced on these plates are shown in Table 4. The difference in height $h_2$-$h_1$ is also shown in Table 4.

The nonwoven materials A, B, C and D produced on plates 1, 2, 3 and 4 are a nonwoven material comprising two layers. The first layer contains 100% by weight of polyethylene terephthalate and has a weight per unit area of 25 g/m$^2$.

The fibre coarseness is 1.7 dtex, and the fibre length is 38 mm. The second layer contains 72% by weight of lyocell fibres and 28% by weight of polyethylene terephthalate. These fibres also have a coarseness of 1.7 dtex and a length of 38 mm. Nonwoven materials E and F produced on plates 5 and 6 have a fibre composition of 60% by weight of Vigor Fluff sulphate pulp from Korsnäs, 23% by weight of polyester (PET) with a length of 20 mm and a coarseness of 1.7 dtex, and 17% by weight of polypropylene fibres (PP) with a coarseness of 1.7 dtex. The weight per unit area is 80 g/m$^2$.

The heights were measured with a contact-free method of measurement. The equipment used is known as MicroProf and is supplied by FRT (Fries Research & Technology). A sensor H1 is used, and a vertical resolution of 3000 µm was used. The resolution in the vertical sense (z-axis) is 100 nm. A description of the method of measurement follows below.

The test specimen is positioned horizontally on a measurement table, where it is held in place by negative pressure. The surface is then illuminated with focussed white light. A passive lens with high colour deviation spreads out the white light vertically in different colours with different focal points and, accordingly, at different heights above the test specimen. When the focussed light meets a surface, it is reflected optimally unlike the unfocussed light, which has a more diffuse reflection. The optimally reflected light passes via the aforementioned lens and an optical cable into a miniature spectrometer. The miniature spectrometer determines the wavelength (colour) of the reflected light, and the distance between the sensor and the test surface is determined with the help of an internal calibration table. The measurements are performed on an area of 20×20 mm with a resolution of 187 measurement points/cm. The diameter of the light beam (measurement point) under these conditions is 5-6 µm.

Figure 6:
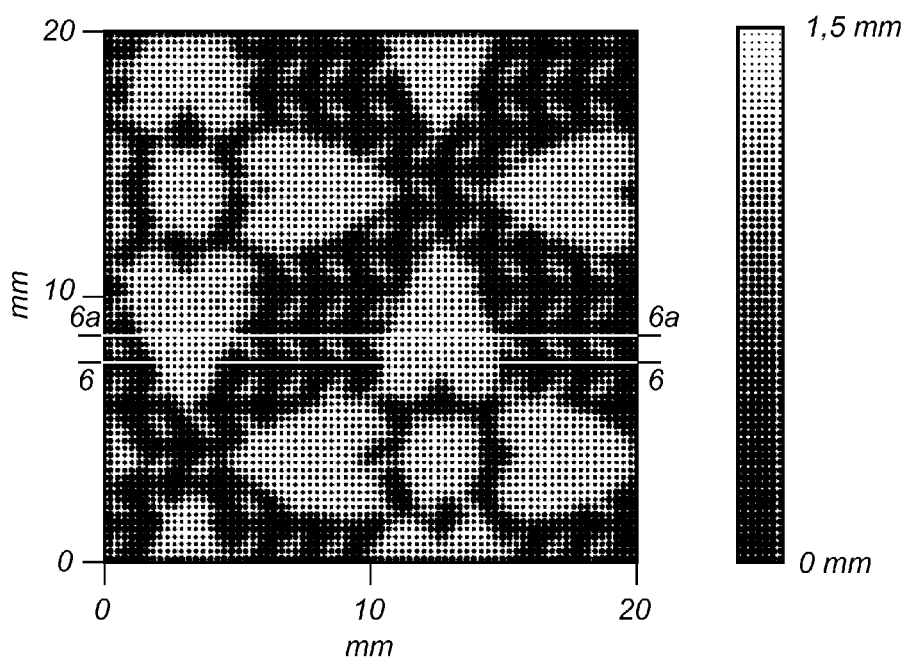
FIG. 6 shows a two-dimensional optical representation of a nonwoven material viewed from above.
Figure 7:
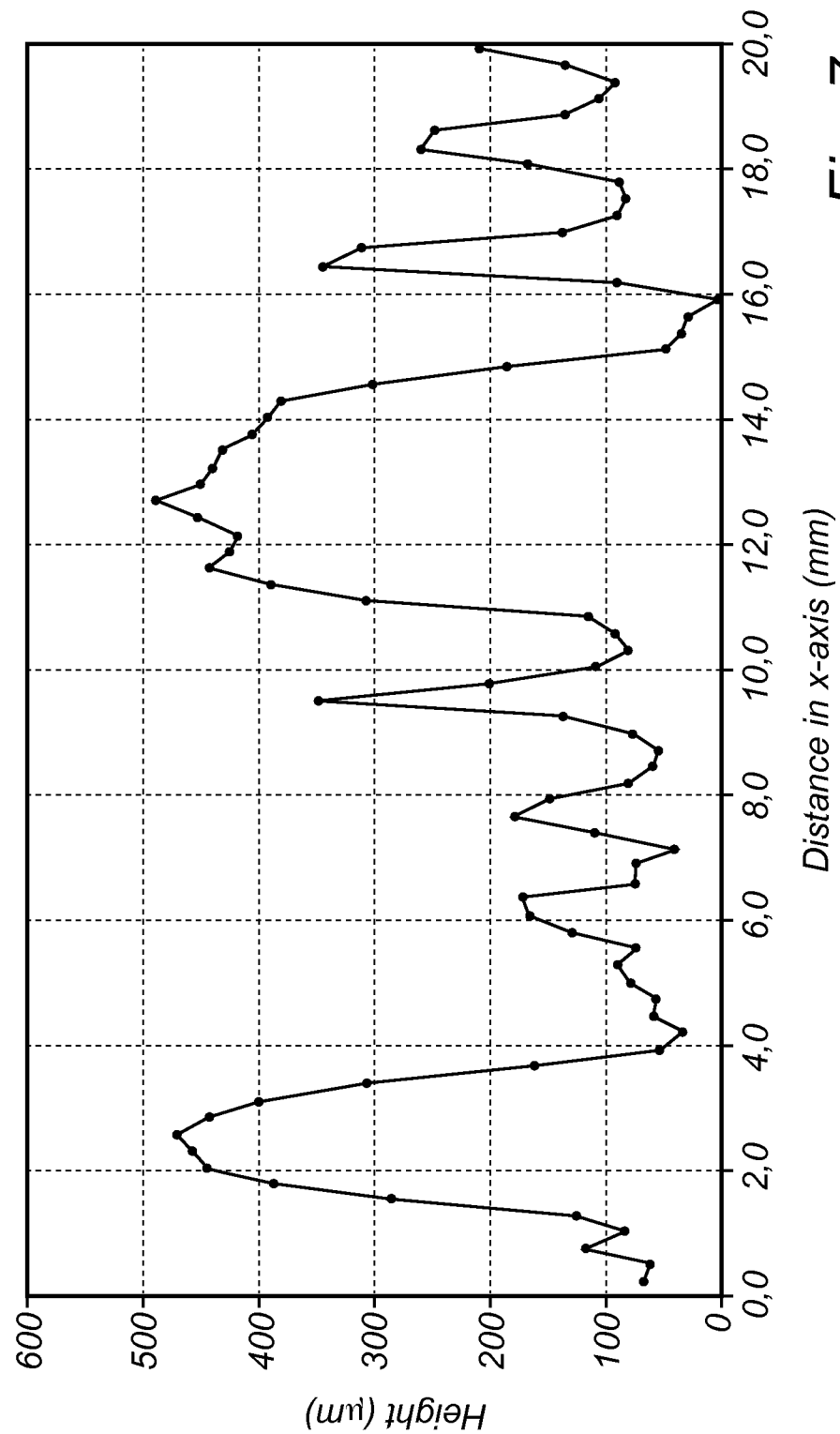
FIG. 7 shows a profile curve of the nonwoven material in the cross section between 6-6 and 6a-6a in FIG. 6.

Every image that illustrates 20×20 mm of the surface of a material is built up of 139876 measurement points, with 374 measurement rows in the y-axis and 374 measurement points on each measurement row. A section of 0.5 mm in the y-axis for the various patterns was studied, that is to say the profile curve, which illustrates differences in height in the material, reflects an area with a width of 0.5 mm in the y-axis. The two-dimensional optical image in FIG. 6 shows an example of how a section is drawn, and the profile curve in FIG. 7 shows the surface profile of the material between the two solid lines 6-6 and 6*a*-6*a*.

In order to avoid the effect of individual fibres and fibre bunches that are oriented in the y-axis of the image and project up from the surface of the material and have nothing to do with the actual surface profile, the individual mean values for y, on which the profile curve is based, have been smoothed in respect of their mean value. This smoothing of the mean value also contributes to eliminating the sharp, deep troughs that occur in the profile curve. These sharp troughs have their origin in hollow spaces between the fibres in the porous nonwoven material, and these, too, have nothing to do with the actual surface profile. Smoothing of the mean value is performed on five mean values for y in the x-axis. Smoothing of the mean value of a greater number of values than five results in a loss of information, that is to say the height of the peaks in the profile curve is lost, and smoothing of the mean value of a smaller number of values than five fails to provide satisfactory elimination of the sharp peaks and the deep troughs that occur. The effect of fibres and fibre bunches that are oriented in the x-axis of the image is eliminated thanks to the fact that the section that is being observed is broader (0.5 mm) than the width of these fibres and fibre bunches. Because the background pattern in certain cases occupies small areas of the base level, a section broader than 0.5 mm should not be selected in view of the associated risk of measuring outside the actual protuberance and the resulting values that are too low.

Profile curves have been drawn at three different points on all of the material images in order to determine the height of the protuberances in the background pattern and the principal pattern. The mean value of these three measurements is shown for the respective materials in the accompanying Table. Profile curves have been drawn on distinct background and principal structures, and the height $h_2$ has been measured here at a maximum height of a lowest protuberance in the profile curve. $h_1$ has been measured at the maximum height of the protuberance in the background structure.

TABLE 1

| | background pattern | | |
|---|---|---|---|
| Plate designation | Form | Area (mm$^2$) Individual holes | Area (mm$^2$) Part image |
| 1 | Ellipse | 0.7 | 2.8 |
| 2 | Ellipse | 0.3 | 0.3 |
| 3 | Ellipse | 0.5 | 0.5 |
| 4 | Ellipse | 0.5 | 0.5 |
| 5 | Ellipse | 0.4 | 0.4 |
| 6 | Circle | 0.5 | 0.5 |

Plate 3 is shown in FIG. 4, and plate 5 is shown in FIG. 5.

TABLE 2 principal pattern

| Plate designation | Form | Area (mm²) Individual holes | Area (mm²) Part image |
|---|---|---|---|
| 1 | Flower comprising six elements, circle in the middle | 11 | 46 |
| 2 | Five sectors of a circle form a flower | 4 | 20 |
| 3 | Flower comprising six equally large circles | 6 | 36 |
| 4 | Flower comprising six elements, circle in the middle | 7 | 29 |
| 5 | Flower comprising four hearts, circle in the middle | 10 | 45 |
| 6 | Small flower comprising 2 irregular ovals + circle in the middle | 14 | 27 |

TABLE 3

Size relationship between principal pattern and background pattern

| Plate designation | Individual/individual |
|---|---|
| 1 | 16 |
| 2 | 13 |
| 3 | 12 |
| 4 | 14 |
| 5 | 25 |
| 6 | 28 |

TABLE 4

Result for nonwoven material

| Designation, nonwoven material | Plate designation on which nonwoven material has been hydroentangled | Height $h_1$ of protuberances in the first surface structure (µm above $h_0$)* | Height $h_2$ of protuberances in the second surface structure (µm above $h_0$)* | Difference $h_2 - h_1$ |
|---|---|---|---|---|
| A | 1 | 351 | 759 | 408 |
| B | 2 | 299 | 474 | 175 |
| C | 3 | 363 | 643 | 280 |
| D | 4 | 542 | 921 | 379 |
| E | 5 | 230 | 435 | 205 |
| F | 6 | 304 | 465 | 161 |

*$h_0$ is the zero level, i.e. the base level of the nonwoven material on the side that has protuberances In the protuberances in the principal structure, the height $h_2$ has been measured on the protuberance that has the lowest height on the profile curve. The height $h_1$ in the background structure is measured on the protuberance that has the highest height on the profile curve. The heights $h_1$ vary from 230 µm to 542 µm, whereas the heights $h_2$ vary from 435 µm to 921 µm.

Figure 8:
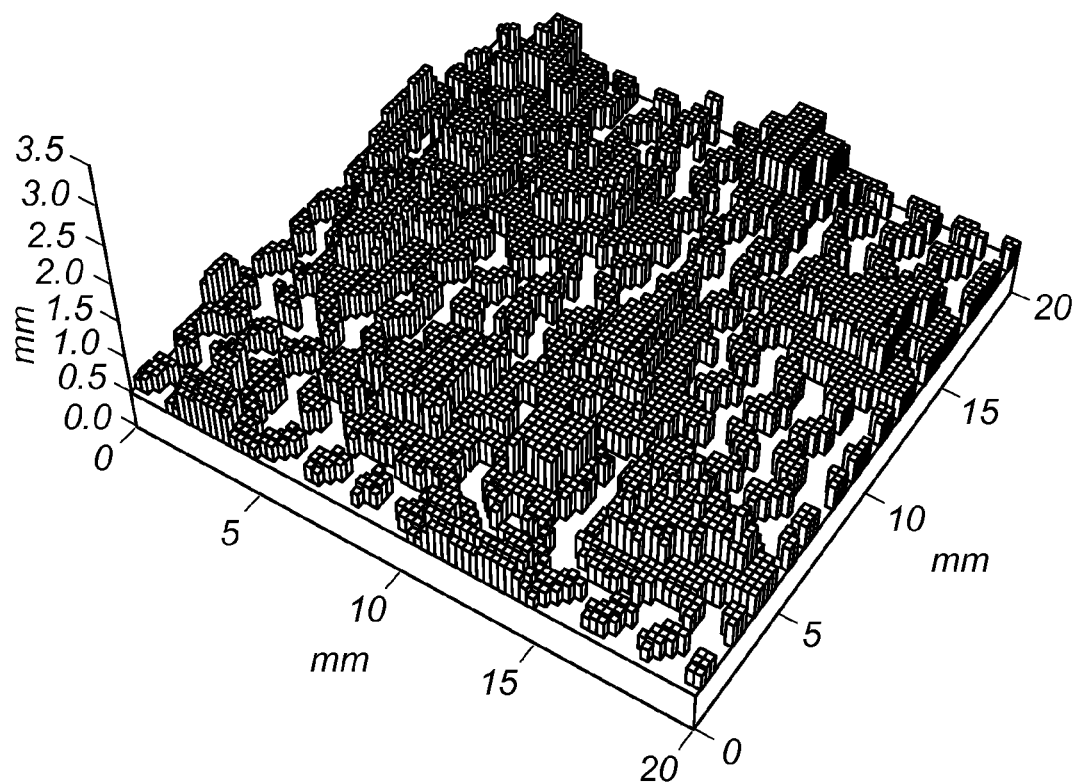
FIG. 8 shows a three-dimensional optical representation of the nonwoven material viewed at an angle from above.

Shown in FIGS. 6 to 8 are the results of the measurements for one of the nonwoven materials. The nonwoven material has been hydroentangled on a plate with the designation 5, as can be seen in FIG. 5. Shown in FIG. 6 is a two-dimensional optical representation of the height measurement for the nonwoven material E, while FIG. 8 shows a three-dimensional optical representation of the nonwoven material E viewed at an angle from above. The surface structure can be seen clearly and corresponds to the pattern that is shown on the plate from FIG. 5. A height profile for the same nonwoven material E is shown in FIG. 7.

Images and surface structures have previously been hydroentangled in nonwoven material, although no image has been created in which different surface structures with different heights, $h_1$ and $h_2$ respectively, have been produced, and in which the protuberances in the surface structures occupy areas of different sizes on the base level of the nonwoven material, where the second protuberances are at least four times larger than the first protuberances. The nonwoven material in accordance with the invention is essentially smooth, moreover, on the second side. A strong nonwoven material with very good wiping-up characteristics, a good absorption capacity and distinct patterns is obtained through the present invention.

The invention claimed is:

1. A method for producing a nonwoven material, comprising the following steps:
    a) providing a substrate web comprising natural fibres having a length of less than 10 mm;
    b) providing a surface-shaped carrier device comprising holes which form at least a first and a second pattern in the form of first and second holes respectively, wherein the second holes are larger than the first holes;
    c) transferring the substrate web to the surface-shaped carrier device; and
    d) hydroentangling the substrate web on the carrier device with jets of liquid under high pressure, so that the fibres of the substrate web penetrate down into the holes to form first protuberances in the first holes and second protuberances in the second holes, wherein the second protuberances have a height that is higher than a height of the first protuberances on a first side of the nonwoven material.

2. The method as claimed in claim 1, wherein the second holes are at least 8 times larger than the first holes.

3. The method as claimed in claim 1, wherein the carrier device has additional holes which are larger than the holes in the second patterns.

4. The method as claimed in claim 1, wherein the carrier device has additional holes which are smaller than the holes in the first patterns.

5. The method as claimed in claim 1, wherein the natural fibres of the substrate web provided in step a) comprises pulp fibres.

6. The method as claimed in claim 1, wherein the second holes are at least 4 times larger than the first holes.

7. The method as claimed in claim 1, wherein the substrate web and carrier device provided in steps a) and b) are configured such that, after performing steps c) and d):
    the nonwoven material has a base level $h_0$ with the first protuberances and the second protuberances on one side, the first protuberances exhibit a height $h_1$ from the base level $h_0$, the second protuberances exhibit a height $h_2$ from the base level $h_0$, and there is a difference of at least 100 µm between $h_1$ and $h_2$,
    each of the second protuberances occupies an area of the surface of the base level at least 4 times greater than each of the first protuberances, and
    the fibres include pulp fibres that are present in a higher proportion in the protuberances than in the rest of the nonwoven material.

8. The method as claimed in claim 1, wherein the carrier device provided in step b) is configured such that, after performing steps c) and d), the second side of the nonwoven material is essentially smooth.

9. The method as claimed in claim 1, wherein the substrate web and carrier device provided in steps a) and b) are configured such that, after performing steps c) and d), each of the second protuberances occupies an area of the surface of the base level at least 8 times greater than each of the first protuberances.

10. The method as claimed in claim 1, wherein the substrate web and carrier device provided in steps a) and b) are configured such that, after performing steps c) and d):
the nonwoven material has a base level $h_0$ with the first protuberances and the second protuberances on one side, the first protuberances exhibit a height $h_1$ from the base level $h_0$, the second protuberances exhibit a height $h_2$ from the base level $h_0$, the height $h_1$ being at least 200 µm, and the height $h_2$ being at least 300 µm.

11. The method as claimed in claim 7, wherein the difference between $h_1$ and $h_2$ is at least 200 µm.

12. The method as claimed in claim 7, wherein the substrate web and carrier device provided in steps a) and b) are configured such that, after performing steps c) and d), the nonwoven material has additional protuberances with at least an additional height $h_2^1$ from the base level $h_0$, wherein the height $h_2^1$ of the additional protuberance is higher than $h_2$ and occupies a larger area of the surface of the base level than the second protuberances.

13. The method as claimed in claim 7, wherein the substrate web and carrier device provided in steps a) and b) are configured such that, after performing steps c) and d), the nonwoven material has additional protuberances having at least an additional height $h_1^1$ from the base level $h_0$, wherein the height $h_1^1$ of the additional protuberance is lower than $h_1$ and occupies a smaller area of the surface of the base level than the first protuberances.

14. The method as claimed in claim 1, wherein the substrate web and carrier device provided in steps a) and b) are configured such that, after performing steps c) and d):
the nonwoven material has a base level $h_0$ with the first protuberances and the second protuberances on one side, the first protuberances exhibit a height $h_1$ from the base level $h_0$, the second protuberances exhibit a height $h_2$ from the base level $h_0$, $h_2$ being at least 1.5 times higher than $h_1$.

15. The method as claimed in claim 1, wherein the substrate web provided in step a) further comprises pulp fibres have a length of less than 10 mm.

16. The method as claimed in claim 7, wherein the substrate web provided in step a) consists essentially of continuous filaments, pulp fibres having a length of less than 10 mm, and staple fibres, and wherein the proportion of pulp fibres having a length of less than 10 mm is at least 5% by weight of the substrate web of fibres.

* * * * *